United States Patent
Hatton et al.

(10) Patent No.: US 12,251,509 B2
(45) Date of Patent: *Mar. 18, 2025

(54) VAPORIZER POWER SYSTEM

(71) Applicant: JUUL Labs, Inc., Washington, DC (US)

(72) Inventors: Nicholas J. Hatton, Oakland, CA (US); Val Valentine, San Francisco, CA (US)

(73) Assignee: JUUL Labs, Inc., Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/101,550

(22) Filed: Jan. 25, 2023

(65) Prior Publication Data

US 2023/0201488 A1   Jun. 29, 2023

Related U.S. Application Data

(63) Continuation of application No. 16/657,857, filed on Oct. 18, 2019, now Pat. No. 11,590,296.

(Continued)

(51) Int. Cl.
*A61M 11/04* (2006.01)
*H02M 3/158* (2006.01)

(52) U.S. Cl.
CPC ... *A61M 11/042* (2014.02); *A61M 2205/3368* (2013.01); *A61M 2205/3576* (2013.01);
(Continued)

(58) Field of Classification Search
CPC .... A61M 11/00; A61M 11/04; A61M 11/041; A61M 11/042–048; A61M 2205/3368;
(Continued)

(56) References Cited

U.S. PATENT DOCUMENTS

| | | |
|---|---|---|
| 3,271,719 A | 9/1966 | Ovshinsky |
| 4,947,874 A | 8/1990 | Brooks et al. |

(Continued)

FOREIGN PATENT DOCUMENTS

| | | |
|---|---|---|
| CN | 1548934 A | 11/2004 |
| CN | 101653354 A | 2/2010 |

(Continued)

OTHER PUBLICATIONS

Dittmer, Greg (2008) Synchronous Boost Converters Provide High Voltage without the Heat, Linear technology magazine, 19-37 pages.

(Continued)

*Primary Examiner* — Thienvu V Tran
*Assistant Examiner* — Carlos O Rivera-Perez
(74) *Attorney, Agent, or Firm* — Mintz Levin Cohn Ferris Glovsky and Popeo, P.C.

(57) ABSTRACT

A system includes a converter configured to electrically couple to a power source and to a heating element of a vaporizer atomizer. The converter can be further configured to receive a first voltage from the power source and provide a second voltage to the heating element. The converter can be a direct-current to direct-current converter. A power monitor configured to electrically couple to the heating element, measure a current through the heating element, measure a voltage over the heating element, calculate a power and/or resistance, and output a control signal to the converter. The converter can be configured to be controlled by the control signal to vary the second voltage to maintain a target power or a target temperature over the heating element. Related apparatus, systems, techniques and articles are also described.

20 Claims, 9 Drawing Sheets

Related U.S. Application Data

(60) Provisional application No. 62/915,294, filed on Oct. 15, 2019, provisional application No. 62/748,203, filed on Oct. 19, 2018.

(52) U.S. Cl.
CPC . *A61M 2205/50* (2013.01); *A61M 2205/8206* (2013.01); *A61M 2205/8237* (2013.01); *H02M 3/1582* (2013.01)

(58) Field of Classification Search
CPC .. A61M 2205/3372; A61M 2205/3576; A61M 2205/50; A61M 2205/82; A61M 2205/8206; A61M 2205/8212; A61M 2205/8237; A61M 2205/8243; Y02E 60/00; Y02E 60/10; A24F 40/00; A24F 40/50; A24F 40/51; A24F 40/57; A24F 40/90; A24F 40/46; A24F 40/44; H02M 3/00; H02M 3/02; H02M 3/04–078; H02M 3/10; H02M 3/135; H02M 3/137; H02M 3/139; H02M 3/142; H02M 3/155; H02M 3/1552; H02M 3/156; H02M 3/1563; H02M 3/1566; H02M 3/157; H02M 3/158; H02M 3/1582; H02M 3/1588; H02M 3/335; H02M 1/00; H02M 1/0003; H02M 1/0009; H02M 1/0025; H02M 1/0032; H02M 1/0035; G05B 11/00; G05B 11/01; G05B 11/26; G05B 11/28
USPC ........ 323/222–226, 259, 271–275, 282–285, 323/299–303, 351; 392/386–406; 320/127–136, 139–145, 147, 150–164
See application file for complete search history.

(56) References Cited

U.S. PATENT DOCUMENTS

| | | | |
|---|---|---|---|
| 5,878,752 A | 3/1999 | Adams et al. | |
| 5,894,394 A | 4/1999 | Baba et al. | |
| 7,275,866 B2 | 10/2007 | Tseng | |
| 8,113,855 B2 | 2/2012 | Green et al. | |
| 8,528,569 B1 | 9/2013 | Newton et al. | |
| 8,781,307 B2 | 7/2014 | Buzzetti et al. | |
| 8,961,492 B2 | 2/2015 | Imran et al. | |
| D725,310 S | 3/2015 | Eksouzian | |
| 9,312,687 B2 | 4/2016 | Xiang | |
| 9,549,573 B2 | 1/2017 | Monsees et al. | |
| 9,806,549 B2 | 10/2017 | Liberti et al. | |
| 10,085,481 B2 | 10/2018 | Verleur et al. | |
| 10,159,282 B2 | 12/2018 | Monsees et al. | |
| 10,638,792 B2 | 5/2020 | Christensen et al. | |
| 10,912,333 B2 | 2/2021 | Atkins et al. | |
| 11,590,296 B2 * | 2/2023 | Hatton | A61M 15/06 |
| 2003/0033055 A1 | 2/2003 | McRae et al. | |
| 2004/0050382 A1 | 3/2004 | Goodchild | |
| 2004/0081624 A1 | 4/2004 | Nguyen et al. | |
| 2006/0047368 A1 * | 3/2006 | Maharajh | F22B 37/38 128/200.14 |
| 2007/0277816 A1 | 12/2007 | Morrison et al. | |
| 2009/0230117 A1 | 9/2009 | Fernando et al. | |
| 2011/0155153 A1 | 6/2011 | Thorens et al. | |
| 2012/0048266 A1 | 3/2012 | Alelov | |
| 2012/0160251 A1 | 6/2012 | Hammel et al. | |
| 2012/0223673 A1 | 9/2012 | Chen et al. | |
| 2013/0023850 A1 | 1/2013 | Imran et al. | |
| 2013/0104916 A1 | 2/2013 | Bellinger et al. | |
| 2013/0192615 A1 | 8/2013 | Tucker et al. | |
| 2014/0007891 A1 | 1/2014 | Liu | |
| 2014/0014126 A1 | 1/2014 | Peleg et al. | |
| 2014/0190496 A1 | 7/2014 | Wensley et al. | |
| 2014/0216484 A1 | 8/2014 | Liu | |
| 2014/0261408 A1 | 9/2014 | DePiano et al. | |
| 2014/0261486 A1 | 9/2014 | Potter et al. | |
| 2014/0270727 A1 | 9/2014 | Ampolini et al. | |
| 2014/0299141 A1 | 10/2014 | Flick | |
| 2014/0334804 A1 | 11/2014 | Choi | |
| 2014/0366898 A1 | 12/2014 | Monsees et al. | |
| 2015/0034104 A1 | 2/2015 | Zhou | |
| 2015/0053214 A1 | 2/2015 | Alarcon et al. | |
| 2015/0136158 A1 | 5/2015 | Stevens et al. | |
| 2015/0164138 A1 | 6/2015 | Liu et al. | |
| 2015/0164147 A1 | 6/2015 | Verleur et al. | |
| 2015/0173124 A1 | 6/2015 | Qiu et al. | |
| 2015/0196060 A1 | 7/2015 | Wensley et al. | |
| 2015/0208729 A1 | 7/2015 | Monsees et al. | |
| 2015/0216237 A1 | 8/2015 | Wensley et al. | |
| 2015/0237916 A1 * | 8/2015 | Farine | A24F 40/53 219/492 |
| 2015/0305409 A1 | 10/2015 | Verleur et al. | |
| 2015/0327596 A1 | 11/2015 | Alarcon et al. | |
| 2015/0357608 A1 | 12/2015 | Huang | |
| 2015/0357839 A1 | 12/2015 | Cai et al. | |
| 2015/0359263 A1 | 12/2015 | Bellinger | |
| 2016/0021933 A1 | 1/2016 | Thorens et al. | |
| 2016/0057811 A1 | 2/2016 | Tucker et al. | |
| 2016/0309786 A1 | 2/2016 | Alarcon et al. | |
| 2016/0087469 A1 | 3/2016 | Armstrong | |
| 2016/0174611 A1 | 6/2016 | Monsees et al. | |
| 2016/0192706 A1 | 7/2016 | Kananen | |
| 2016/0255878 A1 | 9/2016 | Huang et al. | |
| 2016/0309780 A1 | 10/2016 | Chen et al. | |
| 2016/0315488 A1 | 10/2016 | Moon | |
| 2016/0360786 A1 | 12/2016 | Bellinger et al. | |
| 2017/0027234 A1 | 2/2017 | Farine et al. | |
| 2017/0049150 A1 | 2/2017 | Xue et al. | |
| 2017/0071257 A1 | 3/2017 | Lin et al. | |
| 2017/0079327 A1 | 3/2017 | Wu et al. | |
| 2017/0112196 A1 | 4/2017 | Sur et al. | |
| 2017/0119052 A1 | 5/2017 | Williams et al. | |
| 2017/0127726 A1 | 5/2017 | Xiang et al. | |
| 2017/0188636 A1 | 7/2017 | Li et al. | |
| 2017/0196263 A1 | 7/2017 | Sur et al. | |
| 2017/0196270 A1 | 7/2017 | Vick et al. | |
| 2017/0251725 A1 | 9/2017 | Buchberger et al. | |
| 2017/0280779 A1 | 10/2017 | Qui et al. | |
| 2017/0290371 A1 | 10/2017 | Davis et al. | |
| 2017/0294804 A1 | 10/2017 | Sur et al. | |
| 2017/0302089 A1 | 10/2017 | Bernauer et al. | |
| 2018/0035714 A1 | 2/2018 | Sur et al. | |
| 2018/0042306 A1 | 2/2018 | Atkins et al. | |
| 2018/0027879 A1 | 3/2018 | Hatton et al. | |
| 2018/0084608 A1 | 3/2018 | Bernauer et al. | |
| 2018/0090945 A1 * | 3/2018 | Langlinais | H02M 3/1582 |
| 2018/0280637 A1 | 5/2018 | Atkins et al. | |
| 2018/0199627 A1 | 7/2018 | Bowen et al. | |
| 2018/0279685 A1 | 10/2018 | Mayle et al. | |
| 2019/0230987 A1 | 8/2019 | Wu et al. | |
| 2019/0373953 A1 | 12/2019 | Atkins et al. | |
| 2019/0387795 A1 | 12/2019 | Fisher et al. | |
| 2020/0000146 A1 | 1/2020 | Anderson et al. | |
| 2020/0022417 A1 | 1/2020 | Atkins et al. | |
| 2020/0037668 A1 | 2/2020 | Robert et al. | |
| 2020/0046033 A1 * | 2/2020 | Robert | A24F 40/50 |
| 2020/0107585 A1 | 4/2020 | Atkins et al. | |
| 2020/0114094 A1 | 4/2020 | Atkins et al. | |
| 2020/0128874 A1 | 4/2020 | Atkins et al. | |

FOREIGN PATENT DOCUMENTS

| | | |
|---|---|---|
| CN | 202760174 U | 3/2013 |
| CN | 103777670 A | 5/2014 |
| CN | 203873004 U | 10/2014 |
| CN | 204905326 U | 12/2015 |
| CN | 106579560 A | 4/2017 |
| CN | 105011375 B | 12/2017 |
| CN | 108463127 A | 8/2018 |
| CN | 109588779 A | 4/2019 |
| CN | 211123806 U | 7/2020 |
| EP | 2895930 A2 | 7/2015 |
| EP | 3092909 A1 | 11/2016 |

(56) References Cited

FOREIGN PATENT DOCUMENTS

| | | |
|---|---|---|
| EP | 2959787 B1 | 4/2021 |
| EP | 3871539 A1 | 9/2021 |
| EP | 3809894 B1 | 6/2023 |
| JP | 2013113551 A | 6/2013 |
| JP | 2014530632 A | 11/2014 |
| JP | 2018505696 A | 3/2018 |
| KR | 20070112908 A | 11/2007 |
| KR | 101162688 B1 | 7/2012 |
| KR | 101667177 B1 | 12/2015 |
| RU | 2609394 C2 | 2/2017 |
| RU | 2637980 C2 | 12/2017 |
| RU | 2643422 C2 | 2/2018 |
| RU | 2646737 C2 | 3/2018 |
| RU | 2654619 C1 | 5/2018 |
| SG | 11201707778 W | 10/2017 |
| TW | 200922096 A | 5/2009 |
| WO | WO-2010118644 A1 | 10/2010 |
| WO | WO-2011137453 A2 | 11/2011 |
| WO | WO-2012085207 A1 | 6/2012 |
| WO | WO-2012120487 A2 | 9/2012 |
| WO | WO-2013004453 A2 | 1/2013 |
| WO | WO-2013060781 A1 | 5/2013 |
| WO | WO-2013120565 A3 | 3/2014 |
| WO | WO-2014040988 A1 | 3/2014 |
| WO | WO-2014102091 A1 | 7/2014 |
| WO | WO-2014144678 A2 | 9/2014 |
| WO | WO-2014166121 A1 | 10/2014 |
| WO | WO-2015071682 A1 | 5/2015 |
| WO | WO-2015100361 A1 | 7/2015 |
| WO | WO-2015137815 A1 | 9/2015 |
| WO | WO-2015165747 A1 | 11/2015 |
| WO | WO-2016050247 A1 | 4/2016 |
| WO | WO-2016058187 A1 | 4/2016 |
| WO | WO-2016082136 A1 | 6/2016 |
| WO | WO-2016101200 A1 | 6/2016 |
| WO | WO-2016145634 A1 | 9/2016 |
| WO | WO-2017020220 A1 | 2/2017 |
| WO | WO-2017072705 A2 | 5/2017 |
| WO | WO-2017085242 A1 | 5/2017 |
| WO | WO-2018055761 A1 | 3/2018 |
| WO | WO-2018122411 A1 | 7/2018 |
| WO | WO-2018153171 A1 | 8/2018 |
| WO | WO-2018202403 A1 | 11/2018 |
| WO | WO-2020006305 A1 | 1/2020 |
| WO | WO-2020084756 A1 | 4/2020 |

OTHER PUBLICATIONS (Jun. 15, 2021) How to Measure Resistance—Hioki, https://www.hioki.com/en/learning/methods/resistancemeasurement-methods.html/.

Low Level Measurements Handbook—7th Edition Precision DC Current, Voltage, and Resistance Measurements.

(Jun. 15, 2021) Resistance thermometer, https://en.wikipedia.org/wiki/Resistance_thermometer.

(Jun. 15, 2021) Room temperature, https://en.wikipedia.org/wiki/Room_temperature.

Tony R. Kuphaldt (2006) "Temperature coefficient of resistance", Lessons in Electric Circuits, vol. 1 DC, section 12.6.

(Sep. 2011) Linear Technology Data Sheet and Product Info for LTC3786 Low IQ Synchronous Boost Controller, Revision A, Available online at: https://cdn.ozdisan.com/ETicaret_Dosya/482058_5551574.pdf, 34 pages.

* cited by examiner

VAPORIZER POWER SYSTEM

CROSS REFERENCE

The present application claims priority to U.S. patent application Ser. No. 16/657,857 entitled "Vaporizer Power System" filed on Oct. 18, 2019, which claims priority to U.S. Provisional Patent Application No. 62/748,203 entitled "Powering Vapor Atomizer" filed on Oct. 19, 2018, and claims priority to U.S. Provisional Patent Application No. 62/915,294 entitled "Powering Vapor Atomizer" filed on Oct. 15, 2019, each of which are hereby incorporated by reference in their entirety.

TECHNICAL FIELD

The subject matter described herein relates to powering a vaporizer atomizer utilizing a direct-current to direct-current converter.

BACKGROUND

Vaporizer devices, which can also be referred to as vaporizers, electronic vaporizer devices, or e-vaporizer devices, can be used for delivery of an aerosol (for example, a vapor-phase and/or condensed-phase material suspended in a stationary or moving mass of air or some other gas carrier) containing one or more active ingredients by inhalation of the aerosol by a user of the vaporizing device. For example, electronic nicotine delivery systems (ENDS) include a class of vaporizer devices that are battery powered and that can be used to simulate the experience of smoking, but without burning of tobacco or other substances. Vaporizers are gaining increasing popularity both for prescriptive medical use, in delivering medicaments, and for consumption of tobacco, nicotine, and other plant-based materials. Vaporizer devices can be portable, self-contained, and/or convenient for use.

In use of a vaporizer device, the user inhales an aerosol, colloquially referred to as "vapor," which can be generated by a heating element that vaporizes (e.g., causes a liquid or solid to at least partially transition to the gas phase) a vaporizable material, which can be liquid, a solution, a solid, a paste, a wax, and/or any other form compatible for use with a specific vaporizer device. The vaporizable material used with a vaporizer can be provided within a cartridge for example, a separable part of the vaporizer device that contains vaporizable material) that includes an outlet (for example, a mouthpiece) for inhalation of the aerosol by a user.

To receive the inhalable aerosol generated by a vaporizer device, a user may, in certain examples, activate the vaporizer device by taking a puff, by pressing a button, and/or by some other approach. A puff as used herein can refer to inhalation by the user in a manner that causes a volume of air to be drawn into the vaporizer device such that the inhalable aerosol is generated by a combination of the vaporized vaporizable material with the volume of air.

An approach by which a vaporizer device generates an inhalable aerosol from a vaporizable material involves heating the vaporizable material in a vaporizer atomizer or vaporization chamber (e.g., a heater chamber) to cause the vaporizable material to be converted to the gas (or vapor) phase. A vaporizer atomizer or vaporization chamber can refer to an area or volume in the vaporizer device within which a heat source (for example, a conductive, convective, and/or radiative heat source) causes heating of a vaporizable material to produce a mixture of air and vaporized material to form a vapor for inhalation of the vaporizable material by a user of the vaporization device.

Vaporizer atomizers can be used to evaporate liquid into aerosol and may require power and temperature control of a heating element, such as a resistive wire coil, to generate consistent vapor and to prevent liquid degradation from exposure to high temperatures. Typically, two parameters related to heating that may be controlled include electrical power to the heating element and temperature of the heating element.

In a typical vaporizer atomizer, the heater coil can be constructed from a conductor with positive Temperature Coefficient of Resistance (TCR), so that its resistance increases with increase of its bulk temperature. The control loop measures the increase in resistance from ambient to hot and regulates power to the heater to maintain target operating temperature for consistent vapor. Heater power control can be implemented with Pulse Width Modulation (PWM), where electrical current to the heating element is switched ON and OFF at fast rate to control the electrical power dissipated in the element as heat.

While this PWM approach can control a heating element, implementations can be intolerant to large variations in heater and pod contact resistance, can require power to be interrupted to measure heater resistance, can result in shorter battery run time, can result in shorter run time at lower temperatures, can result in faster battery aging, can result in limited system integration, can result in limited TCR, and can result in added component count and cost to measure heater resistance.

SUMMARY

In certain aspects of the current subject matter, challenges associated with powering vaporizer devices may be addressed by inclusion of one or more of the features described herein or comparable/equivalent approaches as would be understood by one of ordinary skill in the art. Aspects of the current subject matter relate to methods and system for powering a heating element of a vaporizer device.

The details of one or more variations of the subject matter described herein are set forth in the accompanying drawings and the description below. Other features and advantages of the subject matter described herein will be apparent from the description and drawings, and from the claims. The claims that follow this disclosure are intended to define the scope of the protected subject matter. In some variations, one or more of the following features may optionally be included in any feasible combination.

In an aspect, a system includes a converter configured to electrically couple to a power source and to a heating element of a vaporizer atomizer. The converter can be further configured to receive a first voltage from the power source and provide a second voltage to the heating element. The converter can be a direct-current to direct-current converter. A power monitor can be configured to electrically couple to the heating element, measure a current through the heating element, measure a voltage over the heating element, calculate a power and/or resistance, and output a control signal to the converter. The converter can be configured to be controlled by the control signal to vary the second voltage to maintain a target power or a target temperature over the heating element.

One or more of the following features can be included in any feasible combination. For example, the converter can include a step-up and/or a step-down converter. The converter can include an energy storage device. The energy storage device can include capacitors in a switched-capacitors topology or a charge-pump topology. The energy storage device can include an inductor. The power monitor can include analog circuitry forming a closed-loop control. The power monitor can include an analog front end circuitry configured to measure the current through the heating element and the voltage over the heating element, and a digitizer including circuitry configured to provide the control signal based on the measured current through the heating element and the measured voltage over the heating element. The digitizer can be configured to provide the control signal as a pulse width modulated signal, a digital to analog converted signal, or an inter-integrated circuit formatted signal. The power monitor can include a 4-wire connection to measure voltage over the heating element. The power monitor can alternatively include a 3-wire connection to measure voltage over the heating element. The power monitor can measure the current and the voltage continuously without interrupting power to the heating element. A microcontroller and a switch can be included between the converter and the heating element. The switch can electrically couple to the microcontroller. The microcontroller can be configured to apply a pulse width modulated signal to a gate of the switch. The converter can be configured to operate at a first power level, and the microcontroller can be configured to determine, based on the measured current through the heating element and the measured voltage over the heating element, a second power level and modify the pulse width modulation signal to control the switch to modify the second voltage.

The converter can be configured to provide power uninterrupted to the heating element during a heating cycle. The power monitor can be configured to determine, based on variations in the measured current, a variation in a contact resistance of a contact between the converter and the heating element. The system can further include a current source configured to couple to the heating element, the current source including a current source resistor and a current source switch.

The system can further include a universal serial bus port including a universal serial bus power rail, the converter configured to output a third voltage to the universal serial bus power rail. The system including the converter can also include a pulse width modulation (PWM) control circuit configured to electrically couple to the power source and to the heating element of the vaporizer atomizer. The pulse width modulation control circuit further configured to provide PWM power to the heating element. The power source can be a battery.

In another aspect, an integrated converter includes the converter, power monitor, and charger in one unit. The converter can be configured to electrically couple to a power source and to a heating element of a vaporizer atomizer. The converter can be further configured to receive a first voltage from the power source and provide a second voltage to the heating element. The converter is a direct-current to direct-current converter. The power monitor can be configured to electrically couple to the heating element, measure a current through the heating element, measure a voltage over the heating element, calculate a power and/or a resistance, and output a control signal to the converter. The charger can be configured to electrically couple to the power source to charge the power source. The converter is configured to be controlled by the control signal to vary the second voltage to maintain a target power or a target temperature over the heating element. The converter and the charger can include an inductor in common to power the heating element and to charge the power source.

In another aspect, a method includes measuring a current through a heating element of a vaporizer atomizer, measuring a voltage over the heating element, calculating a power and/or resistance, and controlling operation of the converter to vary the second voltage to maintain a target power or a target temperature over the heating element. The current can be supplied by a converter configured to electrically couple to a power source and to the heating element. The converter can be further configured to receive a first voltage from the power source and to provide a second voltage to the heating element. The converting being a direct-current to direct-current converter.

One or more of the following features can be included in any feasible combination. For example, the converter can include a step-up and/or a step-down converter; the converter can include an energy storage device. The energy storage device can include capacitors in a switched-capacitors topology or a charge-pump topology. The energy storage device can include an inductor. A control signal can be provided to the converter as a pulse width modulated signal, a digital to analog converted signal, or an inter-integrated circuit formatted signal. A pulse width modulated signal can be applied to a gate of a switch coupled between a microcontroller, the converter, and the heating element. The converter can be configured to operate at a first power level, and the microcontroller is configured to determine, based on the measured current through the heating element and the measured voltage over the heating element, a second power level and modify the pulse width modulation signal to control the switch to modify the second voltage. The converter can be configured to provide power uninterrupted to the heating element during a heating cycle. A variation in a contact resistance of a contact between the converter and the heating element can be determined based on variations in the measured current.

The voltage over the heating element can be measured using a 4-wire connection. The voltage over the heating element can alternatively be measured using a 4-wire connection. The current through the heating element can be continuously measured without interrupting power to the heating element. The voltage over the heating element can be continuously measured without interrupting power to the heating element. The power source can be a battery.

The details of one or more variations of the subject matter described herein are set forth in the accompanying drawings and the description below. Other features and advantages of the subject matter described herein will be apparent from the description and drawings, and from the claims.

BRIEF DESCRIPTION OF DRAWINGS

The accompanying drawings, which are incorporated into and constitute a part of this specification, show certain aspects of the subject matter disclosed herein and, together with the description, help explain some of the principles associated with the disclosed implementations. In the drawings.

When practical, similar reference numbers denote similar structures, features, or elements. Like reference symbols in the various drawings indicate like elements.

DETAILED DESCRIPTION

Figure 1A:
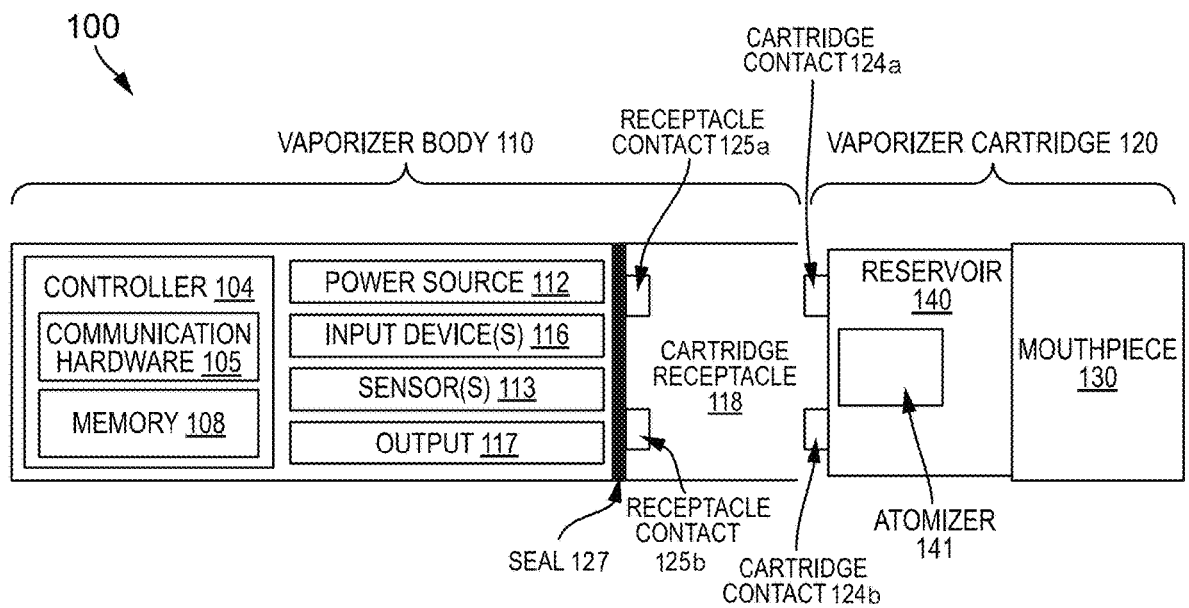
FIG. 1A is a block diagram of a vaporizer device.

Implementations of the current subject matter include methods, apparatuses, articles of manufacture, and systems relating to vaporization of one or more materials for inhalation by a user. Example implementations include methods of powering vaporizer devices and systems including vaporizer devices. The term "vaporizer device" as used in the following description and claims refers to any of a self-contained apparatus, an apparatus that includes two or more separable parts (for example, a vaporizer body that includes a battery and other hardware, and a cartridge that includes a vaporizable material), and/or the like. Vaporizer devices, which can also be referred to as vaporizers, electronic vaporizer devices, or e-vaporizer devices, can be used for delivery of an aerosol (for example vapor-phase and/or condensed-phase material suspended in a stationary or moving mass of air or some other gas carrier) containing one or more active ingredients by inhalation of the aerosol by a user of the vaporizing device. A "vaporizer system," as used herein, can include one or more components, such as a vaporizer device. Examples of vaporizer devices consistent with implementations of the current subject matter include electronic vaporizers, electronic nicotine delivery systems (ENDS), and/or the like. In general, such vaporizer devices are hand-held devices that heat (such as by convection, conduction, radiation, and/or some combination thereof) a vaporizable material to provide an inhalable dose of the material. The vaporizable material used with a vaporizer device can be provided within a cartridge (for example, a part of the vaporizer that contains the vaporizable material in a reservoir or other container) which can be refillable when empty, or disposable such that a new cartridge containing additional vaporizable material of a same or different type can be used). A vaporizer device can be a cartridge-using vaporizer device, a cartridge-less vaporizer device, or a multi-use vaporizer device capable of use with or without a cartridge. For example, a vaporizer device can include a heating chamber (for example, an oven or other region in which material is heated by a heating element) configured to receive a vaporizable material directly into the heating chamber, and/or a reservoir or the like for containing the vaporizable material. In some implementations, a vaporizer device can be configured for use with a liquid vaporizable material (for example, a carrier solution in which an active and/or inactive ingredient(s) are suspended or held in solution, or a liquid form of the vaporizable material itself), a paste, a wax, and/or a solid vaporizable material. A solid vaporizable material can include a plant material that emits some part of the plant material as the vaporizable material (for example, some part of the plant material remains as waste after the material is vaporized for inhalation by a user) or optionally can be a solid form of the vaporizable material itself, such that all of the solid material can eventually be vaporized for inhalation. A liquid vaporizable material can likewise be capable of being completely vaporized, or can include some portion of the liquid material that remains after all of the material suitable for inhalation has been vaporized.

Referring to the block diagram of FIG. 1A, a vaporizer device 100 can include a power source 112 (for example, a battery, which can be a rechargeable battery), and a controller 104 (for example, a processor, circuitry, etc. capable of executing logic) for controlling delivery of heat to an atomizer 141 to cause a vaporizable material 102 to be converted from a condensed form (such as a solid, a liquid, a solution, a suspension, a part of an at least partially unprocessed plant material, etc.) to the gas phase. The controller 104 can be part of one or more printed circuit boards (PCBs) consistent with certain implementations of the current subject matter. After conversion of the vaporizable material 102 to the gas phase, at least some of the vaporizable material 102 in the gas phase can condense to form particulate matter in at least a partial local equilibrium with the gas phase as part of an aerosol, which can form some or all of an inhalable dose provided by the vaporizer device 100 during a user's puff or draw on the vaporizer device 100. It should be appreciated that the interplay between gas and condensed phases in an aerosol generated by a vaporizer device 100 can be complex and dynamic, due to factors such as ambient temperature, relative humidity, chemistry, flow conditions in airflow paths (both inside the vaporizer and in the airways of a human or other animal), and/or mixing of the vaporizable material 102 in the gas phase or in the aerosol phase with other air streams, which can affect one or more physical parameters of an aerosol. In some vaporizer devices, and particularly for vaporizer devices configured for delivery of volatile vaporizable materials, the inhalable dose can exist predominantly in the gas phase (for example, formation of condensed phase particles can be very limited).

The atomizer 141 in the vaporizer device 100 can be configured to vaporize a vaporizable material 102. The vaporizable material 102 can be a liquid. Examples of the vaporizable material 102 include neat liquids, suspensions, solutions, mixtures, and/or the like. The atomizer 141 can include a wicking element (i.e., a wick) configured to convey an amount of the vaporizable material 102 to a part of the atomizer 141 that includes a heating element (not shown in FIG. 1A).

For example, the wicking element can be configured to draw the vaporizable material 102 from a reservoir 140 configured to contain the vaporizable material 102, such that the vaporizable material 102 can be vaporized by heat delivered from a heating element. The wicking element can also optionally allow air to enter the reservoir 140 and replace the volume of vaporizable material 102 removed. In some implementations of the current subject matter, capillary action can pull vaporizable material 102 into the wick for vaporization by the heating element, and air can return to the reservoir 140 through the wick to at least partially equalize pressure in the reservoir 140. Other methods of allowing air back into the reservoir 140 to equalize pressure are also within the scope of the current subject matter.

As used herein, the terms "wick" or "wicking element" include any material capable of causing fluid motion via capillary pressure.

The heating element can include one or more of a conductive heater, a radiative heater, and/or a convective heater. One type of heating element is a resistive heating element, which can include a material (such as a metal or alloy, for example a nickel-chromium alloy, or a non-metallic resistor) configured to dissipate electrical power in the form of heat when electrical current is passed through one or more resistive segments of the heating element. In some implementations of the current subject matter, the atomizer 141 can include a heating element which includes a resistive coil or other heating element wrapped around, positioned within, integrated into a bulk shape of, pressed into thermal contact with, or otherwise arranged to deliver heat to a wicking element, to cause the vaporizable material 102 drawn from the reservoir 140 by the wicking element to be vaporized for subsequent inhalation by a user in a gas and/or a condensed (for example, aerosol particles or droplets) phase. Other wicking elements, heating elements, and/or atomizer assembly configurations are also possible.

Certain vaporizer devices may, additionally or alternatively, be configured to create an inhalable dose of the vaporizable material 102 in the gas phase and/or aerosol phase via heating of the vaporizable material 102. The vaporizable material 102 can be a solid-phase material (such as a wax or the like) or plant material (for example, tobacco leaves and/or parts of tobacco leaves). In such vaporizer devices, a resistive heating element can be part of, or otherwise incorporated into or in thermal contact with, the walls of an oven or other heating chamber into which the vaporizable material 102 is placed. Alternatively, a resistive heating element or elements can be used to heat air passing through or past the vaporizable material 102, to cause convective heating of the vaporizable material 102. In still other examples, a resistive heating element or elements can be disposed in intimate contact with plant material such that direct conductive heating of the plant material occurs from within a mass of the plant material, as opposed to only by conduction inward from walls of an oven.

The heating element can be activated in association with a user puffing (i.e., drawing, inhaling, etc.) on a mouthpiece 130 of the vaporizer device 100 to cause air to flow from an air inlet, along an airflow path that passes the atomizer 141 (i.e., wicking element and heating element). Optionally, air can flow from an air inlet through one or more condensation areas or chambers, to an air outlet in the mouthpiece 130. Incoming air moving along the airflow path moves over or through the atomizer 141, where vaporizable material 102 in the gas phase is entrained into the air. The heating element can be activated via the controller 104, which can optionally be a part of a vaporizer body 110 as discussed herein, causing current to pass from the power source 112 through a circuit including the resistive heating element, which is optionally part of a vaporizer cartridge 120 as discussed herein. As noted herein, the entrained vaporizable material 102 in the gas phase can condense as it passes through the remainder of the airflow path such that an inhalable dose of the vaporizable material 102 in an aerosol form can be delivered from the air outlet (for example, the mouthpiece 130) for inhalation by a user.

Activation of the heating element can be caused by automatic detection of a puff based on one or more signals generated by one or more of a sensor 113. The sensor 113 and the signals generated by the sensor 113 can include one or more of: a pressure sensor or sensors disposed to detect pressure along the airflow path relative to ambient pressure (or optionally to measure changes in absolute pressure), a motion sensor or sensors (for example, an accelerometer) of the vaporizer device 100, a flow sensor or sensors of the vaporizer device 100, a capacitive lip sensor of the vaporizer device 100, detection of interaction of a user with the vaporizer device 100 via one or more input devices 116 (for example, buttons or other tactile control devices of the vaporizer device 100), receipt of signals from a computing device in communication with the vaporizer device 100, and/or via other approaches for determining that a puff is occurring or imminent.

As discussed herein, the vaporizer device 100 consistent with implementations of the current subject matter can be configured to connect (such as, for example, wirelessly or via a wired connection) to a computing device (or optionally two or more devices) in communication with the vaporizer device 100. To this end, the controller 104 can include communication hardware 105. The controller 104 can also include a memory 108. The communication hardware 105 can include firmware and/or can be controlled by software for executing one or more cryptographic protocols for the communication.

A computing device can be a component of a vaporizer system that also includes the vaporizer device 100, and can include its own hardware for communication, which can establish a wireless communication channel with the communication hardware 105 of the vaporizer device 100. For example, a computing device used as part of a vaporizer system can include a general-purpose computing device (such as a smartphone, a tablet, a personal computer, some other portable device such as a smartwatch, or the like) that executes software to produce a user interface for enabling a user to interact with the vaporizer device 100. In other implementations of the current subject matter, such a device used as part of a vaporizer system can be a dedicated piece of hardware such as a remote control or other wireless or wired device having one or more physical or soft (i.e., configurable on a screen or other display device and selectable via user interaction with a touch-sensitive screen or some other input device like a mouse, pointer, trackball, cursor buttons, or the like) interface controls. The vaporizer device 100 can also include one or more outputs 117 or devices for providing information to the user. For example, the outputs 117 can include one or more light emitting diodes (LEDs) configured to provide feedback to a user based on a status and/or mode of operation of the vaporizer device 100.

In the example in which a computing device provides signals related to activation of the resistive heating element, or in other examples of coupling of a computing device with the vaporizer device 100 for implementation of various control or other functions, the computing device executes one or more computer instruction sets to provide a user interface and underlying data handling. In one example, detection by the computing device of user interaction with one or more user interface elements can cause the computing device to signal the vaporizer device 100 to activate the heating element to reach an operating temperature for creation of an inhalable dose of vapor/aerosol. Other functions of the vaporizer device 100 can be controlled by interaction of a user with a user interface on a computing device in communication with the vaporizer device 100.

The temperature of a resistive heating element of the vaporizer device 100 can depend on a number of factors, including an amount of electrical power delivered to the resistive heating element, conductive heat transfer to other parts of the electronic vaporizer device 100 and/or to the environment, latent heat losses due to vaporization of the vaporizable material 102 from the wicking element and/or the atomizer 141 as a whole, and convective heat losses due to airflow (i.e., air moving across the heating element or the atomizer 141 as a whole when a user inhales on the vaporizer device 100). As noted herein, to reliably activate the heating element or heat the heating element to a desired temperature, the vaporizer device 100 may, in some implementations of the current subject matter, make use of signals from the sensor 113 (for example, a pressure sensor) to determine when a user is inhaling. The sensor 113 can be positioned in the airflow path and/or can be connected (for example, by a passageway or other path) to an airflow path containing an inlet for air to enter the vaporizer device 100 and an outlet via which the user inhales the resulting vapor and/or aerosol such that the sensor 113 experiences changes (for example, pressure changes) concurrently with air passing through the vaporizer device 100 from the air inlet to the air outlet. In some implementations of the current subject matter, the heating element can be activated in association with a user's puff, for example by automatic detection of the puff, or by the sensor 113 detecting a change (such as a pressure change) in the airflow path.

The sensor 113 can be positioned on or coupled to (i.e., electrically or electronically connected, either physically or via a wireless connection) the controller 104 (for example, a printed circuit board assembly or other type of circuit board). To take measurements accurately and maintain durability of the vaporizer device 100, it can be beneficial to provide a seal 127 resilient enough to separate an airflow path from other parts of the vaporizer device 100. The seal 127, which can be a gasket, can be configured to at least partially surround the sensor 113 such that connections of the sensor 113 to the internal circuitry of the vaporizer device 100 are separated from a part of the sensor 113 exposed to the airflow path. In an example of a cartridge-based vaporizer, the seal 127 can also separate parts of one or more electrical connections between the vaporizer body 110 and the vaporizer cartridge 120. Such arrangements of the seal 127 in the vaporizer device 100 can be helpful in mitigating against potentially disruptive impacts on vaporizer components resulting from interactions with environmental factors such as water in the vapor or liquid phases, other fluids such as the vaporizable material 102, etc., and/or to reduce the escape of air from the designated airflow path in the vaporizer device 100. Unwanted air, liquid or other fluid passing and/or contacting circuitry of the vaporizer device 100 can cause various unwanted effects, such as altered pressure readings, and/or can result in the buildup of unwanted material, such as moisture, excess vaporizable material 102, etc., in parts of the vaporizer device 100 where they can result in poor pressure signal, degradation of the sensor 113 or other components, and/or a shorter life of the vaporizer device 100. Leaks in the seal 127 can also result in a user inhaling air that has passed over parts of the vaporizer device 100 containing, or constructed of, materials that may not be desirable to be inhaled.

In some implementations, the vaporizer body 110 includes the controller 104, the power source 112 (for example, a battery), one more of the sensor 113, charging contacts (such as those for charging the power source 112), the seal 127, and a cartridge receptacle 118 configured to receive the vaporizer cartridge 120 for coupling with the vaporizer body 110 through one or more of a variety of attachment structures. In some examples, the vaporizer cartridge 120 includes the reservoir 140 for containing the vaporizable material 102, and the mouthpiece 130 has an aerosol outlet for delivering an inhalable dose to a user. The vaporizer cartridge 120 can include the atomizer 141 having a wicking element and a heating element. Alternatively, one or both of the wicking element and the heating element can be part of the vaporizer body 110. In implementations in which any part of the atomizer 141 (i.e., heating element and/or wicking element) is part of the vaporizer body 110, the vaporizer device 100 can be configured to supply vaporizable material 102 from the reservoir 140 in the vaporizer cartridge 120 to the part(s) of the atomizer 141 included in the vaporizer body 110.

Cartridge-based configurations for the vaporizer device 100 that generate an inhalable dose of a vaporizable material 102 that is not a liquid, via heating of a non-liquid material, are also within the scope of the current subject matter. For example, the vaporizer cartridge 120 can include a mass of a plant material that is processed and formed to have direct contact with parts of one or more resistive heating elements, and the vaporizer cartridge 120 can be configured to be coupled mechanically and/or electrically to the vaporizer body 110 that includes the controller 104, the power source 112, and one or more receptacle contacts 125a and 125b configured to connect to one or more corresponding cartridge contacts 124a and 125b and complete a circuit with the one or more resistive heating elements.

In an embodiment of the vaporizer device 100 in which the power source 112 is part of the vaporizer body 110, and a heating element is disposed in the vaporizer cartridge 120 and configured to couple with the vaporizer body 110, the vaporizer device 100 can include electrical connection features (for example, means for completing a circuit) for completing a circuit that includes the controller 104 (for example, a printed circuit board, a microcontroller, or the like), the power source 112, and the heating element (for example, a heating element within the atomizer 141). These features can include one or more contacts (referred to herein as cartridge contacts 124a and 124b) on a bottom surface of the vaporizer cartridge 120 and at least two contacts (referred to herein as receptacle contacts 125a and 125b) disposed near a base of the cartridge receptacle 118 of the vaporizer device 100 such that the cartridge contacts 124a and 124b and the receptacle contacts 125a and 125b make electrical connections when the vaporizer cartridge 120 is inserted into and coupled with the cartridge receptacle 118. The circuit completed by these electrical connections can allow delivery of electrical current to a heating element and can further be used for additional functions, such as measuring a resistance of the heating element for use in determining and/or controlling a temperature of the heating element based on a thermal coefficient of resistivity of the heating element.

In some implementations of the current subject matter, the cartridge contacts 124a and 124b and the receptacle contacts 125a and 125b can be configured to electrically connect in either of at least two orientations. In other words, one or more circuits necessary for operation of the vaporizer device 100 can be completed by insertion of the vaporizer cartridge 120 into the cartridge receptacle 118 in a first rotational orientation (around an axis along which the vaporizer cartridge 120 is inserted into the cartridge receptacle 118 of the vaporizer body 110) such that the cartridge contact 124a is electrically connected to the receptacle contact 125a and the cartridge contact 124b is electrically connected to the receptacle contact 125b. Furthermore, the one or more circuits necessary for operation of the vaporizer device 100 can be completed by insertion of the vaporizer cartridge 120 in the cartridge receptacle 118 in a second rotational orientation such cartridge contact 124a is electrically connected to the receptacle contact 125b and cartridge contact 124b is electrically connected to the receptacle contact 125a.

In one example of an attachment structure for coupling the vaporizer cartridge 120 to the vaporizer body 110, the vaporizer body 110 includes one or more detents (for example, dimples, protrusions, etc.) protruding inwardly from an inner surface of the cartridge receptacle 118, additional material (such as metal, plastic, etc.) formed to include a portion protruding into the cartridge receptacle 118, and/or the like. One or more exterior surfaces of the vaporizer cartridge 120 can include corresponding recesses (not shown in FIG. 1A) that can fit and/or otherwise snap over such detents or protruding portions when the vaporizer cartridge 120 is inserted into the cartridge receptacle 118 on the vaporizer body 110. When the vaporizer cartridge 120 and the vaporizer body 110 are coupled (e.g., by insertion of the vaporizer cartridge 120 into the cartridge receptacle 118 of the vaporizer body 110), the detents or protrusions of the vaporizer body 110 can fit within and/or otherwise be held within the recesses of the vaporizer cartridge 120, to hold the vaporizer cartridge 120 in place when assembled. Such an assembly can provide enough support to hold the vaporizer cartridge 120 in place to ensure good contact between the cartridge contacts 124a and 124b and the receptacle contacts 125a and 125b, while allowing release of the vaporizer cartridge 120 from the vaporizer body 110 when a user pulls with reasonable force on the vaporizer cartridge 120 to disengage the vaporizer cartridge 120 from the cartridge receptacle 118.

In some implementations, the vaporizer cartridge 120, or at least an insertable end 122 of the vaporizer cartridge 120 configured for insertion in the cartridge receptacle 118, can have a non-circular cross section transverse to the axis along which the vaporizer cartridge 120 is inserted into the cartridge receptacle 118. For example, the non-circular cross section can be approximately rectangular, approximately elliptical (i.e., have an approximately oval shape), non-rectangular but with two sets of parallel or approximately parallel opposing sides (i.e., having a parallelogram-like shape), or other shapes having rotational symmetry of at least order two. In this context, approximate shape indicates that a basic likeness to the described shape is apparent, but that sides of the shape in question need not be completely linear and vertices need not be completely sharp. Rounding of both or either of the edges or the vertices of the cross-sectional shape is contemplated in the description of any non-circular cross section referred to herein.

The cartridge contacts 124a and 124b and the receptacle contacts 125a and 125b can take various forms. For example, one or both sets of contacts can include conductive pins, tabs, posts, receiving holes for pins or posts, or the like. Some types of contacts can include springs or other features to facilitate better physical and electrical contact between the contacts on the vaporizer cartridge 120 and the vaporizer body 110. The electrical contacts can optionally be gold-plated, and/or include other materials.

Figure 1B:
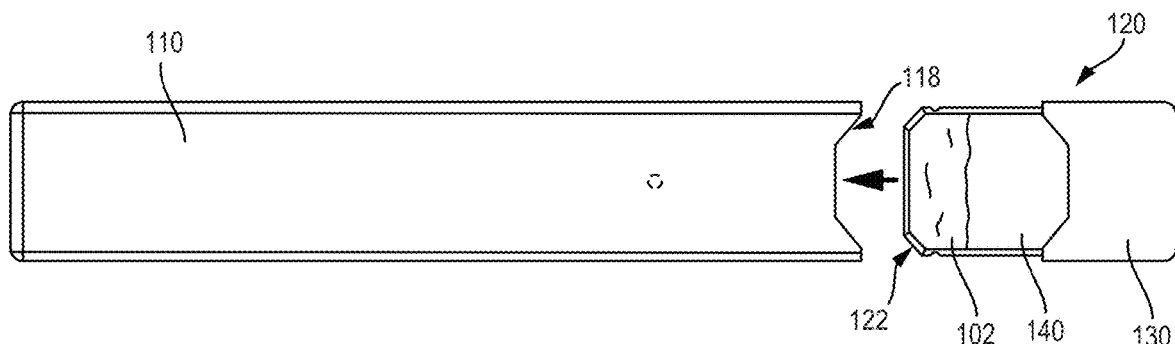
FIG. 1B is a schematic representation of a vaporizer device and vaporizer cartridge.

FIG. 1B illustrates an embodiment of the vaporizer body 110 and the cartridge receptacle 118 into which the vaporizer cartridge 120 can be releasably inserted. FIG. 1B shows a top view of the vaporizer device 100 illustrating the vaporizer cartridge 120 positioned for insertion into the vaporizer body 110. When a user puffs on the vaporizer device 100, air can pass between an outer surface of the vaporizer cartridge 120 and an inner surface of the cartridge receptacle 118 on the vaporizer body 110. Air can then be drawn into the insertable end 122 of the cartridge, through the vaporization chamber that includes or contains the heating element and wick, and out through an outlet of the mouthpiece 130 for delivery of the inhalable aerosol to a user. The reservoir 140 of the vaporizer cartridge 120 can be formed in whole or in part from translucent material such that a level of the vaporizable material 102 is visible within the vaporizer cartridge 120. The mouthpiece 130 can be a separable component of the vaporizer cartridge 120 or can be integrally formed with other component(s) of the vaporizer cartridge 120 (for example, formed as a unitary structure with the reservoir 140 and/or the like).

Further to the discussion above regarding the electrical connections between the vaporizer cartridge 120 and the vaporizer body 110 being reversible such that at least two rotational orientations of the vaporizer cartridge 120 in the cartridge receptacle 118 are possible, in some embodiments of the vaporizer device 100, the shape of the vaporizer cartridge 120, or at least a shape of the insertable end 122 of the vaporizer cartridge 120 that is configured for insertion into the cartridge receptacle 118, can have rotational symmetry of at least order two. In other words, the vaporizer cartridge 120 or at least the insertable end 122 of the vaporizer cartridge 120 can be symmetrical upon a rotation of 180° around an axis along which the vaporizer cartridge 120 is inserted into the cartridge receptacle 118. In such a configuration, the circuitry of the vaporizer device 100 can support identical operation regardless of which symmetrical orientation of the vaporizer cartridge 120 occurs.

Figure 1C:
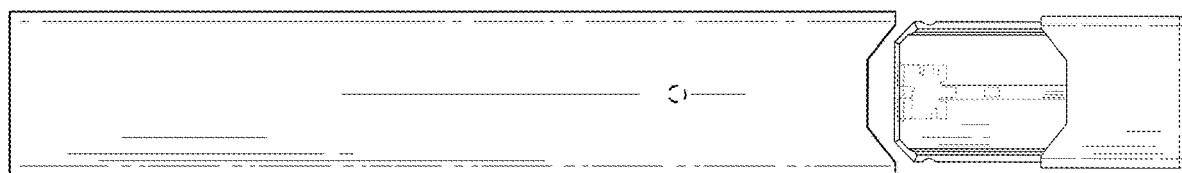
FIG. 1C is a front view of a vaporizer device and an embodiment of a vaporizer cartridge.
Figure 1D:
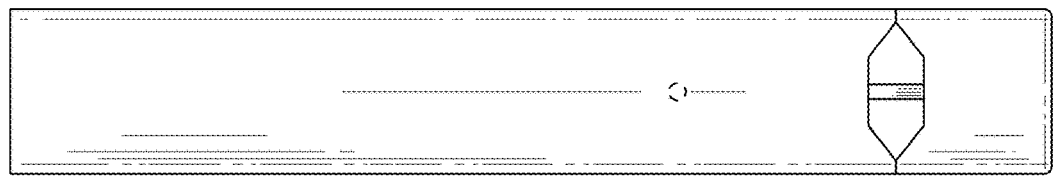
FIG. 1D is a front view of a vaporizer cartridge coupled to a vaporizer device.

FIGS. 1C-1D illustrate example features that can be included in embodiments of the vaporizer device 100 consistent with implementations of the current subject matter. FIGS. 1C and 1D show top views of an example of the vaporizer device 100 before (FIG. 1C) and after (FIG. 1D) connecting the vaporizer cartridge 120 to the vaporizer body 110.

Figure 1E:
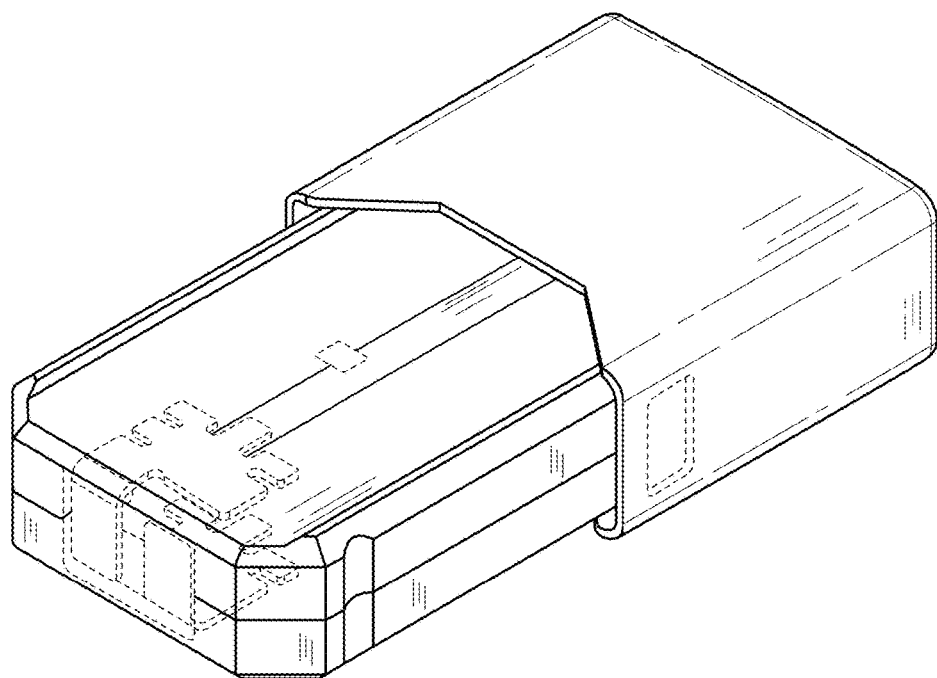
FIG. 1E is a perspective view of a vaporizer cartridge.

FIG. 1E illustrates a perspective view of one variation of the vaporizer cartridge 120 holding the vaporizable material 102. Any appropriate vaporizable material 102 can be contained within the vaporizer cartridge 120 (for example, within the reservoir 140), including solutions of nicotine or other organic materials.

Figure 1F:
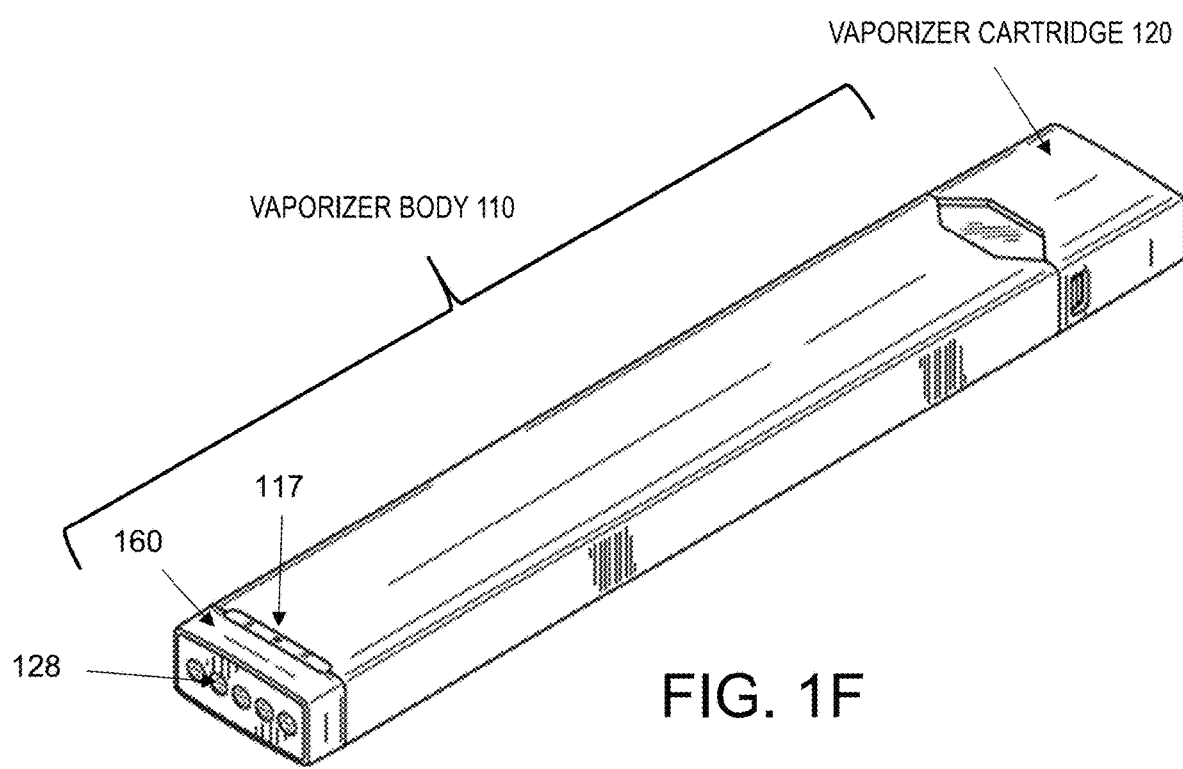
FIG. 1F is a perspective view of another embodiment of a vaporizer cartridge coupled to a vaporizer device.

FIG. 1F shows a perspective view of another example of a vaporizer device 100 including a vaporizer body 110 coupled to a separable vaporizer cartridge 120. As illustrated, the vaporizer device 100 can include one or more outputs 117 (for example, LEDs) configured to provide information to a user based on a status, mode of operation, and/or the like, of the vaporizer device 100. In some aspects, the one or more outputs 117 can include a plurality of LEDs (i.e., two, three, four, five, or six LEDs). The one or more outputs 117 (i.e., each individual LED) can be configured to display light in one or more colors (for example, white, red, blue, green, yellow, etc.). The one or more outputs 117 can be configured to display different light patterns (for example, by illuminating specific LEDs, varying a light intensity of one or more of the LEDs over time, illuminating one or more LEDs with a different color, and/or the like) to indicate different statuses, modes of operation, and/or the like of the vaporizer device 100. In some implementations, the one or more outputs 117 can be proximal to and/or at least partially disposed within a bottom end region 160 of the vaporizer device 100. The vaporizer device 100 may, additionally or alternatively, include externally accessible charging contacts 128, which can be proximate to and/or at least partially disposed within the bottom end region 160 of the vaporizer device 100.

Figure 1G:
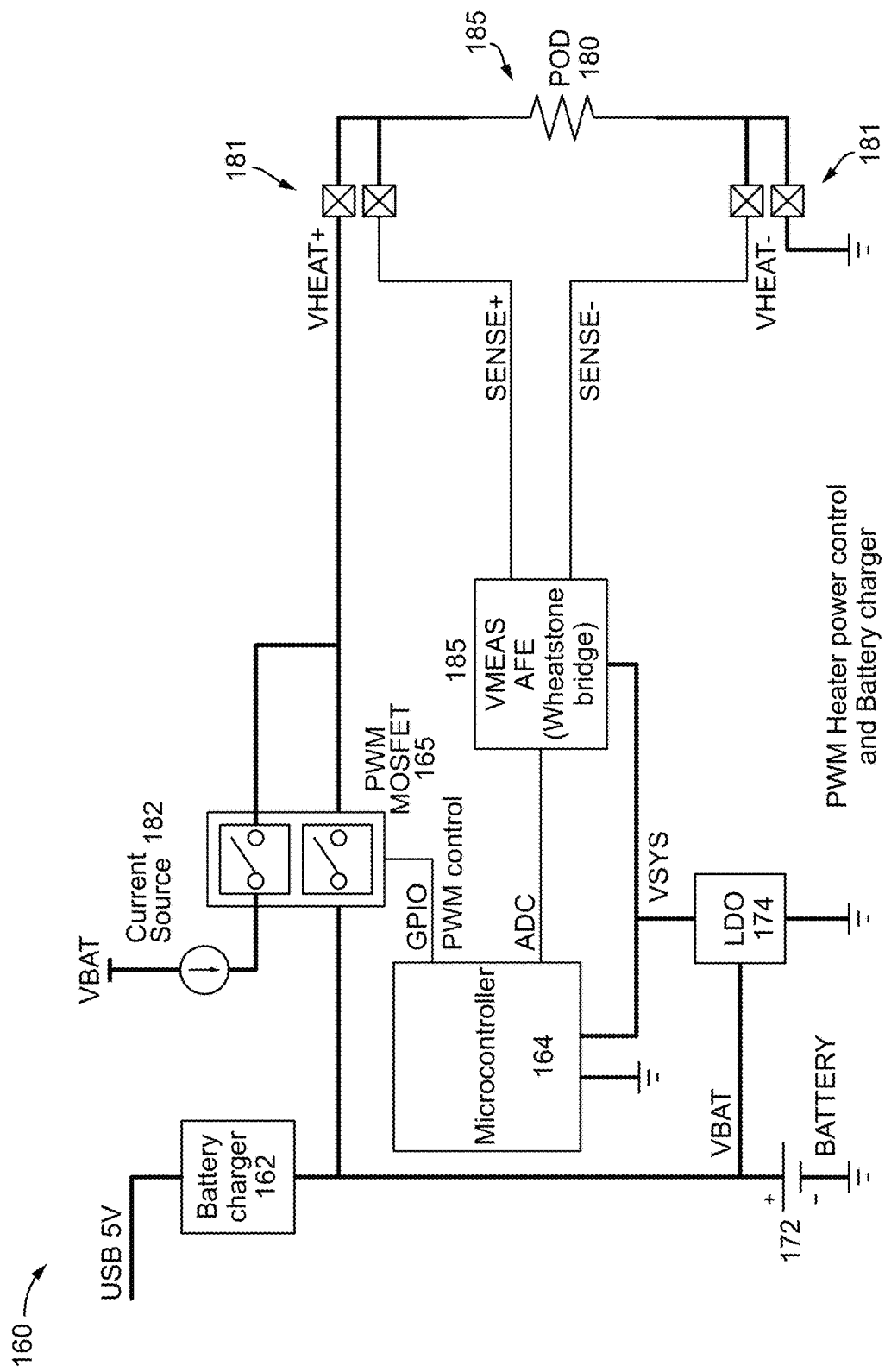
FIG. 1G is a system block diagram illustrating an example PWM heater control.

FIG. 1G is a system block diagram illustrating an example of a conventional PWM heater control 160. The heater control includes a battery charger 162, microcontroller 164, PWM metal-oxide-semiconductor field-effect transistor (MOSFET) 165, voltage measurement point (VMEAS) analog front end (AFE) 185, low-dropout regulator (LDO) 174, and current source 182. The PWM heater control 160 can include contacts 181 for coupling to a pod 180 containing a heating element 185 and vaporizable materials. The PWM heater control 160 can also couple to a battery 172. The microcontroller 164 can control the PWM MOSFET 165 to switch the current source 182 or battery 172 in line with the heating element 185 to provide power to the heating element 185 for heating.

In a conventional PWM control, electrical power is supplied directly from battery 172 and is turned ON and OFF by solid-state switches like PWM MOSFETs 165. The heater resistance can be measured between the PWM pulses by passing known constant current through the heater and measuring the voltage drop over the heating element 185. In some existing vaporizer atomizers, heater control is achieved by pulse width modulation of the power source (e.g., battery) that is being delivered to the heating element. As further explained below, a conventional PWM approach can control a heating element, however, PWM control can be intolerant to large variations in heater and pod contact resistance, can require power to be interrupted to measure heater resistance, can result in shorter battery run time, can result in shorter run time at lower temperatures, can result in faster battery aging, can result in limited system integration, can result in limited TCR, and/or can result in added component count and cost to measure heater resistance.

Some PWM implementations can be intolerant to large variation in heater and pod contact resistance. The PWM control can be limited to the maximum duty cycle. At low battery voltage, PWM control may not compensate for increase in the pod contact resistance to maintain target power. PWM control can require tighter heater resistance tolerances in production to assure the target power in the heater can be reached at low voltage. PWM control can reduced usability, i.e. the user might need to clean the pod contacts often.

PWM control interrupts power to measure the heating element temperature. It can be difficult to measure power over the heater directly, due to PWM switching. For the same reason it can be difficult to measure heater resistance between PWM pulses, so power to the heater is typically interrupted to measure. PWM control can require more complex circuitry, like a stable constant current source and a Wheatstone bridge to measure resistance.

PWM control can result in shorter vaporizer battery run time. There is a minimum battery voltage limit to reach target power. For the example above, the 8.0 W target power requires minimum of about 3.4 V under load. Below about 3.4 V loaded voltage, the PWM duty cycle is at 100% and the system cannot deliver the target power. This will have negative effect on the user experience at low state of charge. With an aged battery, the minimum voltage limit is reached at even higher state of charge resulting in shorter run time.

PWM control can result in shorter vaporizer run time at low temperature. The battery impedance (DCIR) increases at low temperature, even around 15° C. This causes the battery voltage to sag under load and will result in a lower user experience and shorter operating time. At cold temperatures, below 10° C., this effect is greater resulting in much shorter run time.

PWM control can result in faster battery aging. Due to the relatively low heater resistance, the current in the PWM pulses is high at average and high battery voltage. This results in higher polarization in the cell, higher stress, faster aging, and shorter cycle life.

PWM control can result in limited system integration. PWM control charging and heater power control are separate circuits and require larger board area. PWM control can require relatively low resistance of the heating element thus limiting design choices.

PWM control can result limited heater TCR selection options. Higher TCR provides larger resistance change with temperature, larger signal, and thus better temperature measurement accuracy. However, a PWM control can require low TCR to maintain heater power at low battery voltage.

PWM control can result in added component count and added cost to measure heater resistance. For example, the component count may be increased for additional current source and Wheatstone bridge circuitry.

The subject matter described herein provides many technical advantages over conventional PWM control and other heating element control techniques. For example, the current subject matter can enable improved system integration. In some implementations, the charger and heater power control can be built into one DC-DC converter. A single inductor can be used for charging and to power up the heater. Combining the charger and heater control circuits can provide for a cost reduction and/or a space reduction.

In some implementations, the current subject matter can enable reduction in board area, which can allow for larger battery capacity or a smaller overall vaporizer device. Lower overall cost, tolerant to significant variation in heater and pod contact resistance, and the like can be achieved. The output voltage can scale with increase in load resistance to maintain power. This can compensate for large variations in the pod contact resistance and allows for looser production tolerances of the heating element.

In some implementations, the current subject matter can improve usability by automatically compensating for changes in contact resistance, thus requiring cleaning of the contacts less often.

In some implementations, the current subject matter enables measurement of the heater element while heating. For example, uninterrupted power can be provided to the heater while also measuring heater power directly during heating. A simpler measurement circuit can be achieved due to the DC output of the converter.

In some implementations, the current subject matter can enable a longer battery run time, allow a battery cell to discharge deeper under load to 3.0 V or even lower for longer run time within target performance, and/or enable improved performance at low environmental temperature (e.g., in cold weather), for example, the battery voltage can dip at low temperature yet the converter can maintain consistent power to the heater and/or provide a longer run time at the low temperature.

In some implementations, the current subject matter can improve battery cycle life, reduce stress to the battery due to lower peak discharge current, enable higher system integration such as a charger and a heater power control can be built into one integrated DC-DC converter, utilize a same single inductor (i.e. an inductor in common to charger and heater power control) for charging and to power the heating element, and/or reduce board area required by the heater control, which can allow for larger battery capacity or smaller device, and/or lowers overall cost.

Some implementations can achieve less heat dissipation during charging compared to a linear charger, less heat transfer to the charger temperature sensor (typically a negative temperature coefficient (NTC) mounted on the battery cell) allows for accurate battery temperature measurement, enables high charge efficiency from a battery powered charge accessory, and/or saves energy.

Some implementations can provide alternative heater resistance measurement with low excitation current with and no self-heating, which can be implemented by at least adding a resistor in line with the heater and a power FET.

The current subject matter relates to heating control of a vaporizer atomizer using a direct-current to direct-current (DC-DC) converter and a power monitor that can measure current through the heater and voltage over the heating element to calculate power and resistance. The converter's output voltage can be controlled to maintain a target power and/or a target temperature over the heating element. By utilizing a DC-DC converter control, the current subject matter can enable one or more of continuous heater resistance and temperature monitoring while power is varied, providing faster preheat and consistent power profile at low battery voltage and temperature, combining charger and heater control circuits enabling cost and space reduction, compensating for increase in pod contact resistance and improving user experience, allowing for higher heater TCR without overloading the battery when the heating element is near ambient temperature, improving efficiency at low battery voltage, improving battery run time, providing consistent performance at lower temperature; prolonging battery life, and the like.

Figure 2:
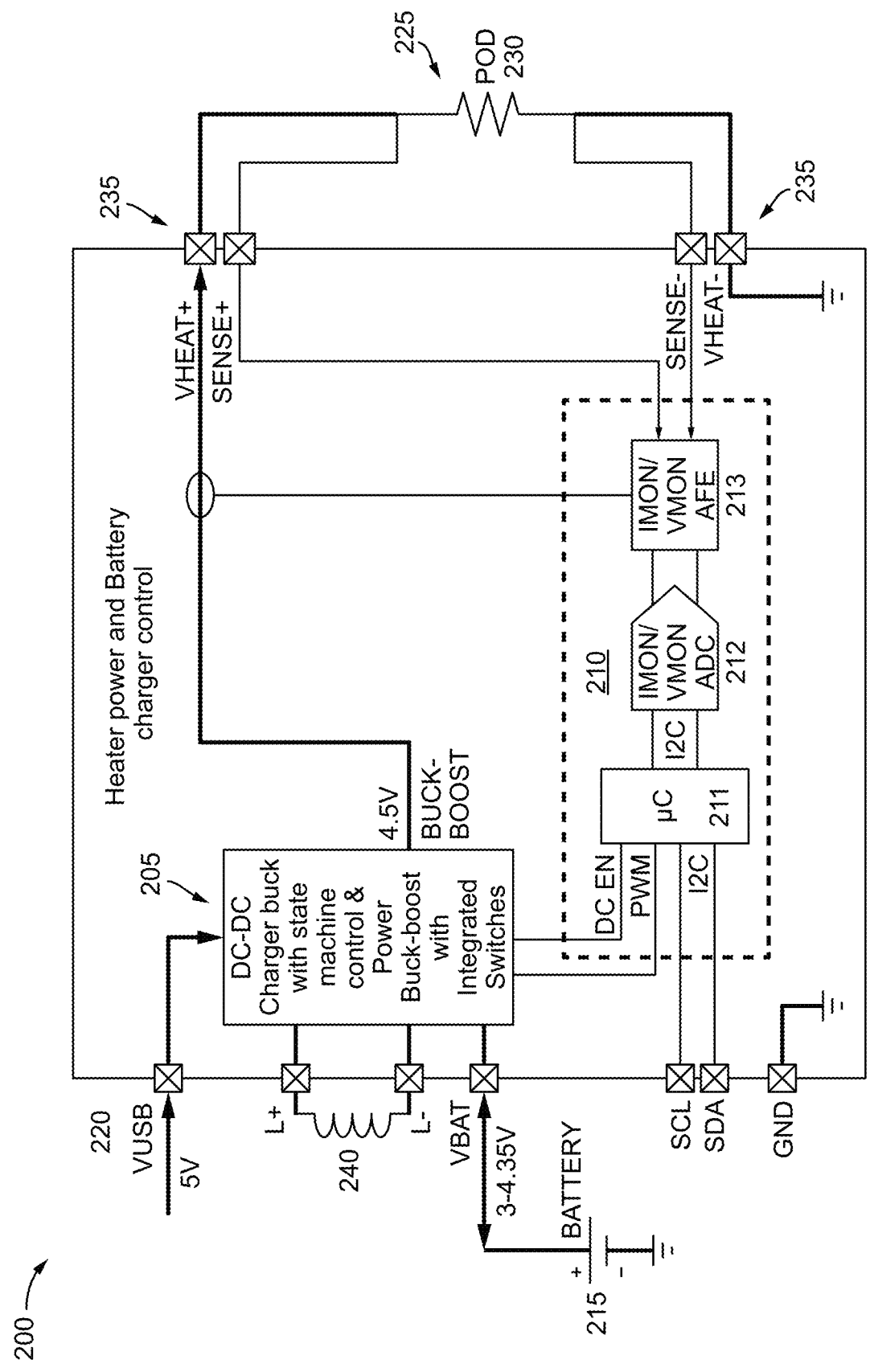
FIG. 2 is a system block diagram illustrating an example heater power control according to some aspects of the current subject matter.

FIG. 2 is a system block diagram illustrating an example heater power control 200 according to some aspects of the current subject matter. The heater power control 200 can include a buck-boost DC-DC converter 205 and power monitor 210. In some implementations, heater power control 200 is part of the circuitry of controller 104 described above.

The converter 205 can electrically couple to a power source (e.g., battery 215 and/or universal serial bus (USB) power 220) and to a heating element 225 residing in a pod 230. The converter 205 can coupled to the heating element 225 via contacts 235. The converter can receive a first voltage (e.g., $V_{BAT}$ or $V_{USB}$) from the power source (e.g., 215 or 220) and provide a second voltage (e.g., $V_{HEAT+}$) to the heating element 225.

The power monitor 210 can electrically couple to the heating element 225 and can include a microprocessor 211, an analog to digital converter 212 and an analog front end 213. The power monitor 210 can measure a current through the heating element 225, measure a voltage over the heating element (e.g., voltage drop from $V_{HEAT+}$ to $V_{HEAT-}$, calculate a power and/or resistance, and output a control signal (e.g., DC EN) to the converter 205).

The converter 205 can be controlled by the control signal (e.g., DC EN) to vary the second voltage (e.g., $V_{HEAT+}$) to maintain a target power or a target temperature over the heating element 225. By maintaining a target power or a target temperature over the heating element 225 utilizing the converter 205 and power monitor 210, improved vaporizer atomizers can be achieved.

In some implementations, converter 205 can include an energy storage component 240. For example, converter 205 can utilize capacitors as an energy storage component 240 in a switched-capacitors or a charge-pump topology. However, to limit the peak current draw from the battery 215 and as illustrated in FIG. 2, converter 205 can include an inductor as an energy storage component 240. An inductor-based converter can be utilized to step down the voltage (e.g., buck), step up the voltage (e.g., boost) or regulate within the battery voltage range (e.g., buck-boost).

In some implementations, a closed loop control of the converter 205 can be realized with power monitor 210 including analog circuitry to measure voltage and current and output analog signal to control the converter. In some implementations, the close loop control (e.g., can be realized with Analog Front End (AFE) circuitry to obtain voltage and current information. The power monitor 210 can include a digital converter 212 with a digital control output signal like PWM, digital to analog converted (DAC) signal, or an inter-integrated circuit formatted signal (I2C). The power monitor 210 can measure voltage across the heating element 225 and current through the heating element 225 to calculate the electrical power dissipated in the heating element 225 and the heating element's 225 resistance. Unlike conventional PWM approaches, this can be performed continuously, without interrupting power to the heating element.

In some implementations, the current subject matter can utilize a 4-wire (Kelvin) connection (e.g., four contacts 235) for accurate voltage measurement over the heating element 225. In some implementations, the current subject matter can utilize a 2-wire pod connection (e.g., two contacts 235) or 3-wire connection.

In some implementations, 5V power can be provided enabling the DC-DC converter 205 to charge other electronic devices from the internal battery 215. In this case, the converter outputs 5V as a USB power source. In this implementation, the converter can operate in one of three modes: 1) as a charger, 2) for heater control or 3) as USB power source.

Some implementations can allow for higher heater TCR. Higher TCR can provide larger ΔR/ΔT signal (change in resistance/change in temperature) and a more accurate temperature measurement. Some implementations can allow for pod contact resistance diagnostic in which variations in the output current can be analyzed to sense increase in contact resistance.

Figure 3:
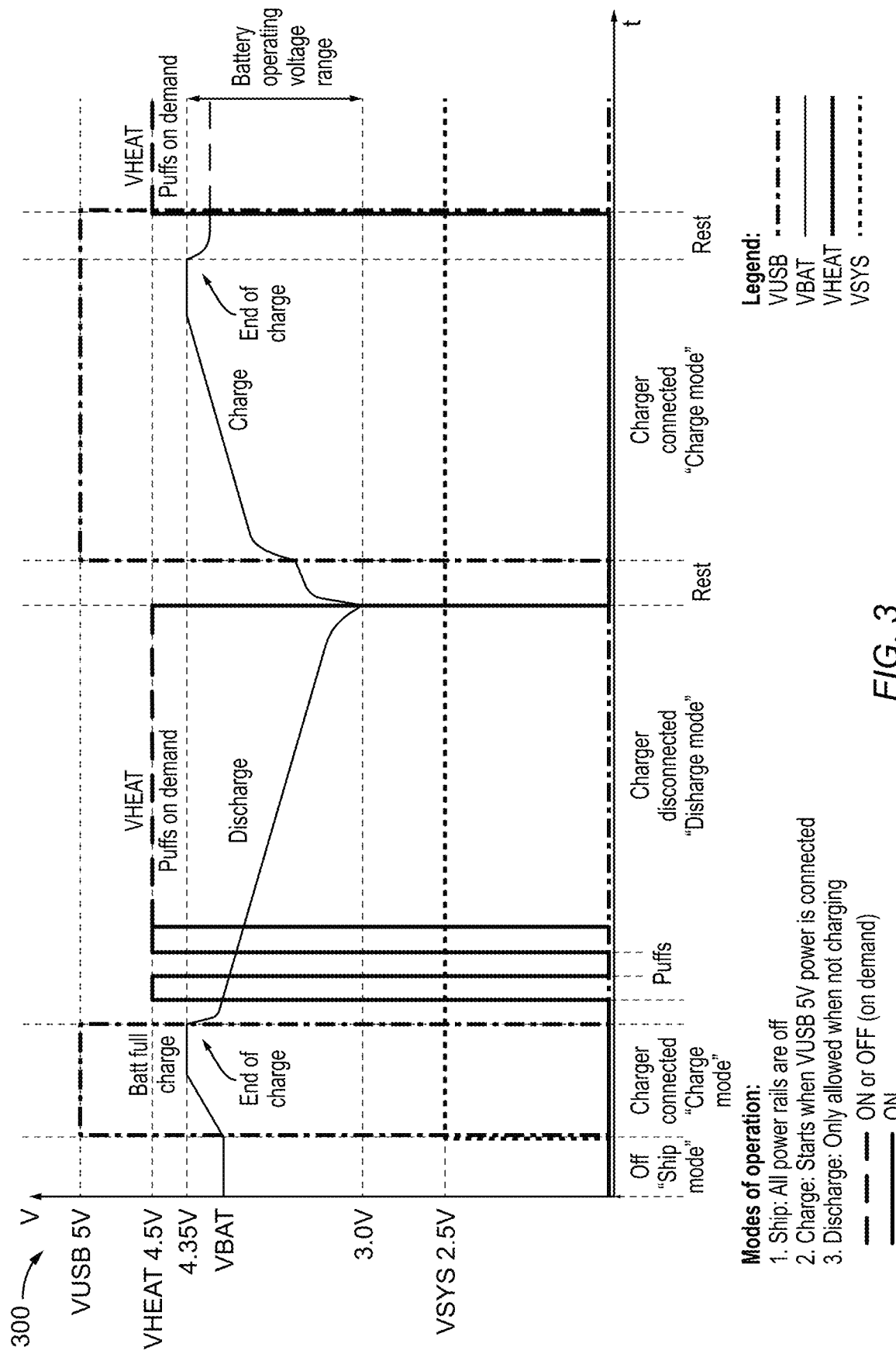
FIG. 3. is a diagram illustrating modes of operation of the example heater control 200 illustrated in FIG. 2.

FIG. 3 is a diagram illustrating modes of operation of the example heater power control 200 illustrated in FIG. 2. Voltage versus time is illustrated for a device in off "ship" mode, when the charger is connected (e.g., charge mode), during puffs, when a charger is disconnected ("discharge mode"), rest, charge mode, and rest.

Figure 4:
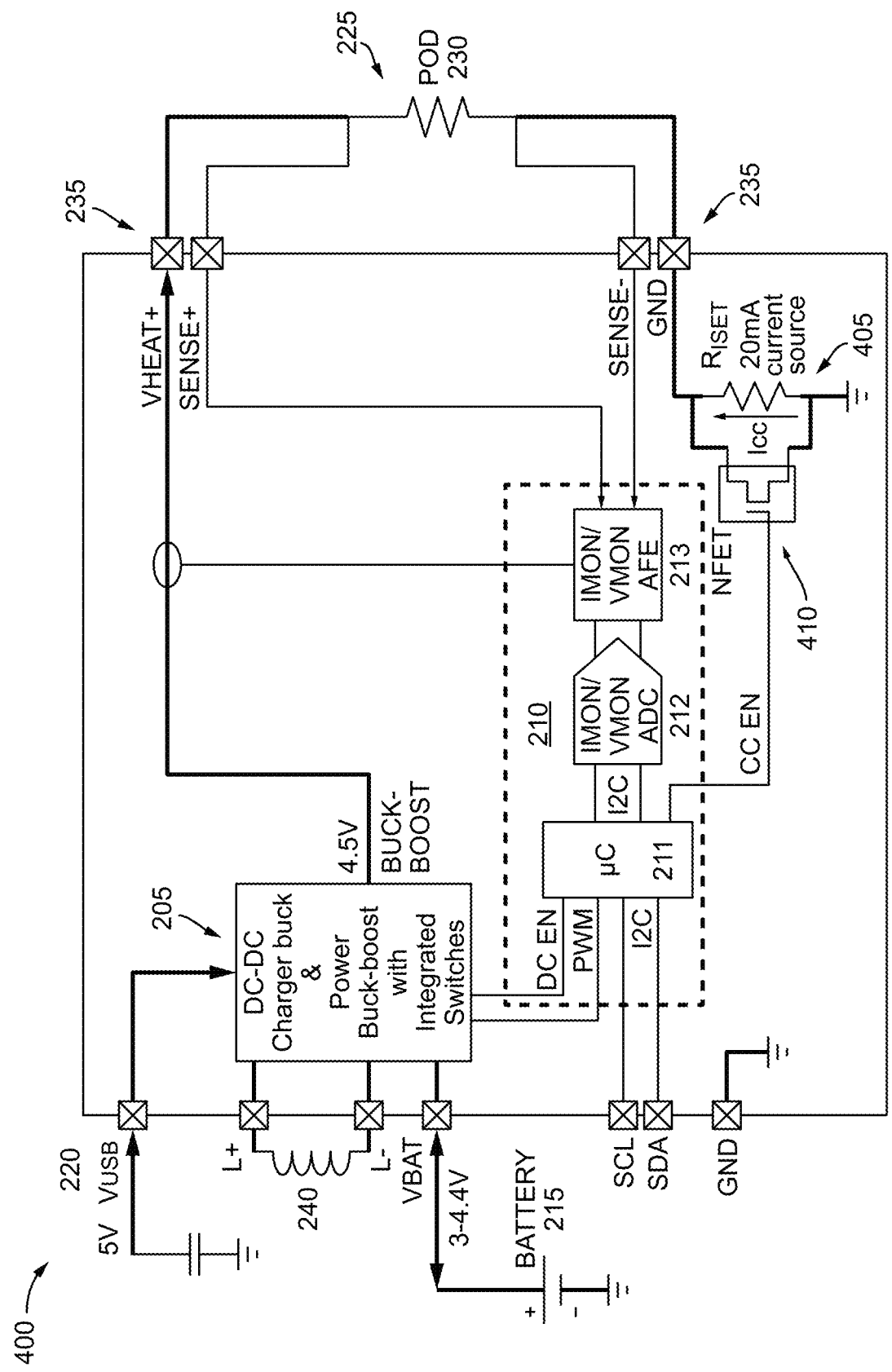
FIG. 4 is a system block diagram illustrating an example heater control in which the converter operates as a current source.

In some implementations, the DC-DC converter can be utilized as a constant current source. In some implementations, the DC-DC converter can provide constant current to measure heater resistance between puffs. This can convert the constant voltage output to a current source. FIG. 4 is a system block diagram illustrating an example heater control 400 in which the converter 205 operates as a current source. The example heater control 400 includes a resistor 405 and switch 410 (MOSFET) located in line with the heating element 225. The switch 410 is controlled by the power monitor 210.

The current can be set by the value $R_{ISET}$ of resistor 405 and, in some implementations, can be chosen around 10-100 mA. The power monitor 210 can measure the voltage across the heating element 225 and the current through the heating element 225 to calculate resistance.

In an example implementation, a heating element 225 can include a positive Temperature Coefficient of Resistance (TCR) of +5% temperature rise at 250° C. above ambient. Heater power can be 8 Watts (W), resistance of heating element 225 ($R_h$)=0.5 ohms (Ω) and parasitic resistance Rp=0.35Ω at operating temperature. The voltage over the heater can be initially set to 2.00 V. As the heating element 225 heats up, its resistance increases to 0.525Ω=0.5Ω*1.05 and the heater voltage also increases to 2.05 V to maintain 8 W over the heater. Note that the actual output voltage of the DC-DC converter is higher, at 2.80 V at start of heating and 2.83 V at target temperature to compensate for the voltage drop over the parasitic resistances.

Assuming a 93% efficient DC-DC converter, the overall efficiency of this DC-DC circuit can be about 56%, or about 15% lower than PWM control, which is described more fully below. To increase efficiency, it can be possible to increase the output voltage to 4.5 V. This can cause $R_h$ to increase to 2.11Ω. The average efficiency increases to about 75%. In this case, the converter efficiency is about 4% higher than the PWM efficiency.

In some implementations, higher heater resistance can be utilized for high efficiency, the power monitor can incorporate filtering to improve voltage and current measurement accuracy, and the current subject matter can utilize converters with improved internal power field-effect transistors (FETs) design for lower on resistance $R_{DS(on)}$ and faster switching to achieve higher efficiency.

In some implementations, a hybrid heater control can be achieved by combining the DC-DC converter with PWM control circuit to improve an overall efficiency of the vaporizer device. For example, PWM can be used at high battery voltage and provide a boost at low battery voltage or low temperature or to compensate for increase in pod contact resistance. The DC-DC converter can be set to operate at a relatively high efficiency (for the DC-DC converter) and can be switched on and off when less than full output power is required. In this manner, the PWM control circuit can supplement the DC-DC converter providing power to the heating element or can solely provide PWM power to the heating element when the DC-DC converter is switched off.

In some implementations, a method of hybrid heater control includes measuring a power source output voltage (for example a battery output voltage) and selecting an operating circuit (for example by using a controller or by using an automatic voltage switch) for powering a heating element. In some implementations, the method includes powering the heating element with a PWM control circuit at the power source output voltage greater than or equal to 4.0 V and powering the heating element with a DC-DC converter control circuit when the power source output voltage less than 4.0 V. In some implementations, the method includes powering the heating element with the PWM control circuit at the power source output voltage greater than or equal to 3.8 V and powering the heating element with the DC-DC converter control circuit when the power source output voltage less than 3.8 V. In some implementations, the method includes powering the heating element with the PWM control circuit at the power source output voltage greater than or equal to 3.6 V and powering the heating element with a DC-DC converter control circuit when the power source output voltage less than 3.6 V. In some implementations, the method includes powering the heating element with a PWM control circuit at the power source output voltage greater than or equal to 3.4 V and powering the heating element with a DC-DC converter control circuit when the power source output voltage less than 3.4 V.

In some implementations, a method of hybrid heater control includes measuring a duty cycle of a PWM control circuit (for example by using a controller) powering a heating element, and switching to a DC-DC converter control circuit to power the heating element when the duty cycle is greater than 85%. In some implementations, the method of hybrid heater control includes measuring a duty cycle of the PWM control circuit (for example by using a controller) powering the heating element, and switching to the DC-DC converter control circuit to power the heating element when the duty cycle is greater than 90%. In some implementations, the method of hybrid heater control includes measuring the duty cycle of a PWM control circuit (for example by using a controller) powering the heating element, and switching to the DC-DC converter control circuit to power the heating element when the duty cycle is greater than 95%. In some implementations, the method of hybrid heater control includes measuring the duty cycle of the PWM control circuit (for example by using a controller) powering the heating element, and switching to the DC-DC converter control circuit to power the heating element when the duty cycle is greater than 98%. In some implementations, a method of hybrid heater control includes measuring a duty cycle of the PWM control circuit (for example by using a controller) powering the heating element, and switching to the DC-DC converter control circuit to power the heating element when the duty cycle is about 100%.

Figure 5:
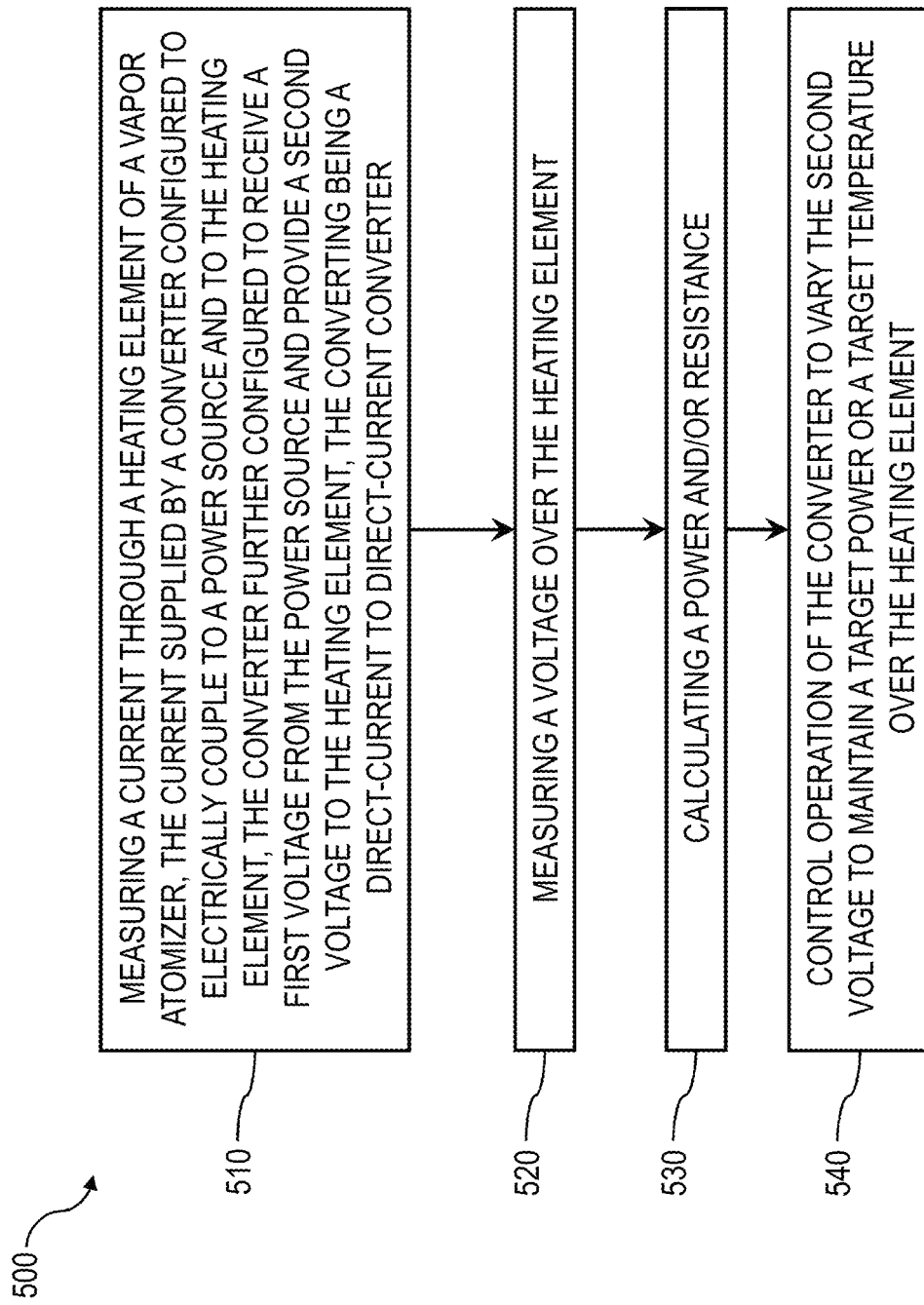
FIG. 5 is a process flow diagram illustrating an example process of operating a heater control according to some aspects of the current subject matter.

FIG. 5 is a process flow diagram illustrating an example process 500 of operating a heater control according to some aspects of the current subject matter. At 510, a current can be measured through a heating element of a vaporizer atomizer. The current can be supplied by a converter configured to electrically couple to a power source and to the heating element. The converter can be further configured to receive a first voltage from the power source and provide a second voltage to the heating element. The converter can be a direct-current to direct-current converter.

At 520, a voltage over the heating element can be measured. At 530, a power and/or resistance can be calculated. At 530 operation of the converter can be controlled to vary the second voltage to maintain a target power or a target temperature over the heating element.

The following includes an example PWM control implementation, which can supplement the DC-DC converter providing power to the heating element or can solely provide PWM power to the heating element when the DC-DC converter is switched off. The operating voltage range of a typical Li-ion battery cell is about 4.2 V to 3.0 V as it discharges from full to empty. To assure sufficient voltage to reach a target power and temperature, the resistance of the heating element (Rh) is chosen for minimum operating voltage at max PWM duty cycle (D). Current and power in the PWM pulses are proportional to voltage and given by Ohm's law Ih=Vb/R, where: Ih is the current, Vb is the battery voltage, and R is the resistance. R includes all resistances in the electrical power path between the chemical cell's positive and negative terminals and the atomizer.

Figure 6:
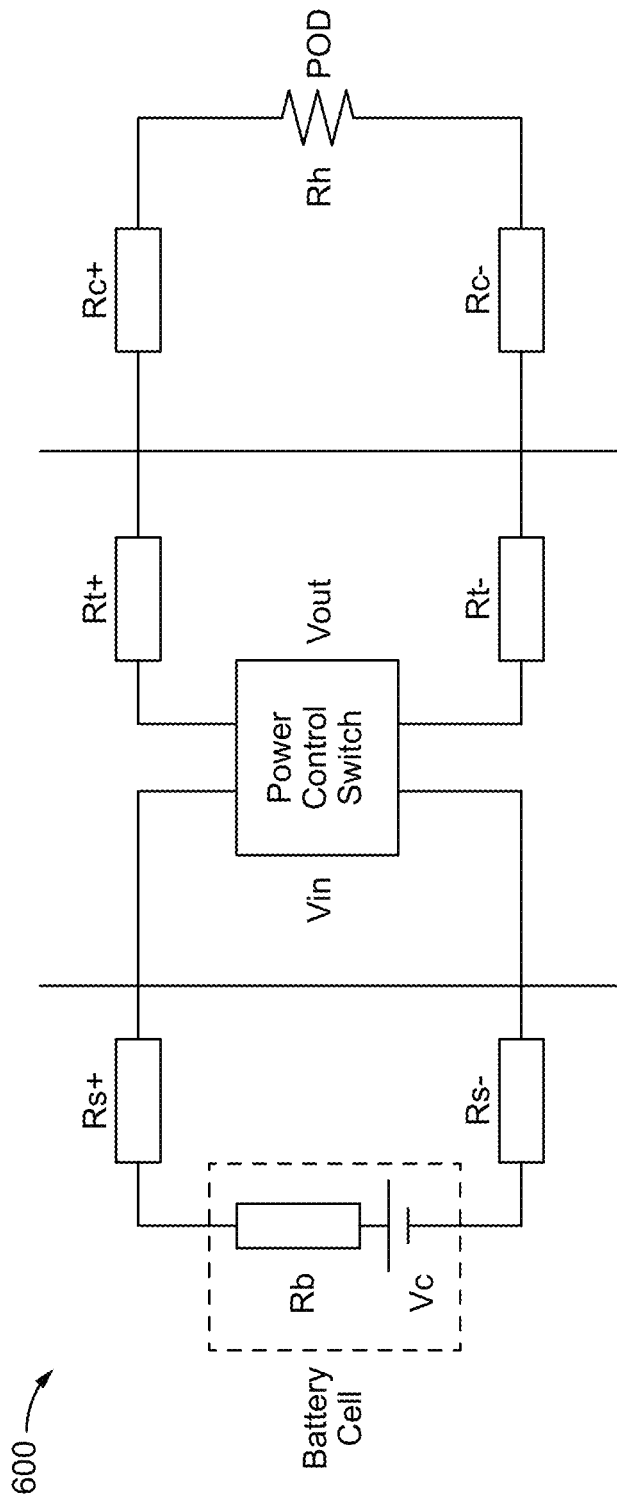
FIG. 6 illustrates an example circuit diagram illustrating resistances and related parameters in an example electrical power path and including a power control switch.

In some implementations, resistance R can be represented as sum of the following resistances: Rb: Internal cell impedance (DCIR); Rs: Battery safety electronics, FETs and PWM switches; Rt: Conductors resistance, wires, PCBA traces, electrical interconnects; Rc: Pod contact resistance; and Rh: Resistive heating element (atomizer). For simplicity, parasitic resistances can be presented as Rp=Rb+Rs+Rt+Rc. Then the total resistance in the circuit is R=Rh+Rp. FIG. 6 illustrates an example circuit diagram illustrating resistances and related parameters in an example electrical power path and including a power control switch. Note that the resistances in the positive and negative rails are represented as a single resistance in the calculations.

For PWM control calculations and for target power of 8.0 W at the heating element, the power from the battery can be represented as $Pb=Ph+Pp$, where: Pb is the power drawn from the battery, Ph is the power over the heating element, and Pp is the power loss over the sum of all parasitic resistances. Similarly, the battery voltage Vb can be represented as a sum of the voltage over the heating element Vh and over the parasitic resistance Vp, as $Vb=Vh+Vp$. $Vh=Rh*I$ and $Vp=Rp*I$ can be substituted to derive $Vb=I*(Rh+Rp)$. Rh can be chosen such as, $Ph \geq 8.0$ W at max duty cycle and minimum battery voltage where $Rb=200$ mΩ (for small Li-ion cell); $Rs=60$ mΩ; $Rt=60$ mΩ; $Rc=30$ mΩ; $Rp=0.35\Omega$.

$R=0.50\Omega$ can be selected at minimum battery voltage of 3.40 V. The total resistance in the circuit is $R=Rp+Rh=0.35\Omega+0.5\Omega=0.85\Omega$. The peak current in the PWM pulses during heating is $I=3.4$ V$/0.85\Omega=4.0$ A. This is the current at different state of charge for the example above: 4 A at minimum battery voltage of 3.4 V; 5.28 A at average battery voltage of 3.7 V; and 6.74 A at maximum battery voltage of 4.2 V. The average power drawn from the battery at 3.70 V is 11.22 W with electrical efficiency of 71.3%. Note that the power losses are independent of the duty cycle, since power to the heating element is delivered only in the PWM pulses.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

Terminology

When a feature or element is herein referred to as being "on" another feature or element, it can be directly on the other feature or element or intervening features and/or elements can also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements can be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature can have portions that overlap or underlie the adjacent feature.

Terminology used herein is for the purpose of describing particular embodiments and implementations only and is not intended to be limiting. For example, as used herein, the singular forms "a," "an," and "the" are intended to include the plural forms as well, unless the context clearly indicates otherwise.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device can be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers can be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value can have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes can be made to various embodiments without departing from the teachings herein. For example, the order in which various described method steps are performed may often be changed in alternative embodiments, and in other alternative embodiments, one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system can include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Use of the term "based on," herein and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described herein can be directed to various combinations and subcombinations of the disclosed features and/or combinations and subcombinations of several further features disclosed herein. In addition, the logic flows depicted in the accompanying figures and/or described herein do not necessarily require the particular order shown, or sequential order, to achieve desirable results. Other implementations may be within the scope of the following claims.

What is claimed is:

1. A method comprising:
    measuring a current through a heating element of a vaporizer atomizer, the current supplied by a converter configured to electrically couple to a power source and to the heating element, the converter further configured to receive a first voltage from the power source and provide a second voltage to the heating element, the converter being a direct-current to direct-current (DC-DC) converter;

measuring a voltage over the heating element;
calculating a power and/or a resistance;
varying the second voltage to maintain a target power or a target temperature over the heating element;
measuring the first voltage from the power source; and
selecting an operating circuit for powering the heating element, wherein the operating circuit is a pulse width modulation control circuit when the first voltage modulated by the pulse width modulation control circuit is sufficient to achieve the target power or the target temperature of the heating element, and wherein the operating circuit is a DC-DC converter control circuit including the DC-DC converter when the first voltage modulated by the pulse width modulation control circuit is not sufficient to achieve the target power or the target temperature of the heating element.

2. The method of claim 1, wherein the first voltage is 4.0 V, 3.8 V, 3.6 V, or 3.4 V.

3. The method of claim 1, wherein measuring the voltage over the heating element includes using a 3-wire connection or a 4-wire connection.

4. The method of claim 1, wherein the DC-DC converter includes a step-up and/or a step-down converter and an energy storage device, wherein the energy storage device includes an inductor and/or capacitors in a switched-capacitors topology or a charge-pump topology.

5. The method of claim 1, wherein measuring the voltage over the heating element occurs without interrupting power to the heating element, and wherein the DC-DC converter is configured to provide power uninterrupted to the heating element during a heating cycle.

6. The method of claim 1, further comprising:
determining, based on variations in the measured current, a variation in a contact resistance of a contact between the DC-DC converter and the heating element.

7. A method comprising:
measuring a current through a heating element of a vaporizer atomizer, the current supplied by a converter configured to electrically couple to a power source and to the heating element, the converter further configured to receive a first voltage from the power source and provide a second voltage to the heating element, the converter being a direct-current to direct-current (DC-DC) converter;
measuring a voltage over the heating element;
calculating a power and/or a resistance;
varying the second voltage to maintain a target power or a target temperature over the heating element;
measuring a duty cycle of a pulse width modulation control circuit;
selecting a DC-DC converter control circuit including the DC-DC converter when the duty cycle required to achieve the target temperature or the target power exceeds a maximum duty cycle of the pulse width modulation control circuit; and
selecting the pulse width modulation control circuit when the duty cycle required to achieve the target temperature or the target power does not exceed the maximum duty cycle of the pulse width modulation control circuit.

8. The method of claim 7, wherein the maximum duty cycle is 85%, 90%, 95%, 98%, or about 100%.

9. The method of claim 7, wherein measuring the voltage over the heating element includes using a 3-wire connection or a 4-wire connection.

10. The method of claim 7, wherein the DC-DC converter includes a step-up and/or a step-down converter and an energy storage device, wherein the energy storage device includes an inductor and/or capacitors in a switched-capacitors topology or a charge-pump topology.

11. The method of claim 7, wherein measuring the voltage over the heating element occurs without interrupting power to the heating element, and wherein the DC-DC converter is configured to provide power uninterrupted to the heating element during a heating cycle.

12. The method of claim 7, further comprising:
determining, based on variations in the measured current, a variation in a contact resistance of a contact between the DC-DC converter and the heating element.

13. A device comprising: circuitry configured to measure a current through a heating element of a vaporizer atomizer, the circuitry further configured to measure a voltage over the heating element of the vaporizer atomizer, the current supplied by a converter configured to electrically couple to a power source and to the heating element, the converter further configured to receive a first voltage from the power source and provide a second voltage to the heating element, the converter being a direct-current to direct-current (DC-DC) converter, the circuitry further configured for calculating a power and/or a resistance, varying the second voltage to maintain a target power or a target temperature over the heating element, and measuring the first voltage from the power source; and a microcontroller configured to select an operating circuit for powering the heating element, wherein the operating circuit is selected to be a pulse width modulation control circuit when the first voltage modulated by the pulse width modulation control circuit is sufficient to achieve the target power or the target temperature of the heating element, or when a duty cycle required to achieve the target temperature or the target power does not exceed a maximum duty cycle of the pulse width modulation control circuit, and wherein the operating circuit is a DC-DC control circuit including the DC-DC converter when the first voltage modulated by the pulse width modulation control circuit is not sufficient to achieve the target power or the target temperature of the heating element, or when the duty cycle required to achieve the target temperature or the target power exceeds the maximum duty cycle of the pulse width modulation control circuit.

14. The device of claim 13, wherein the operating circuit for powering the heating element is selected based on the first voltage, and wherein the operating circuit is the pulse width modulation control circuit when the first voltage is greater than or equal to a selected voltage of 3.4 V to 4.0 V, and wherein the operating circuit is the DC-DC control circuit including the DC-DC converter when the first voltage is less than the selected voltage of 3.4 V to 4.0 V.

15. The device of claim 13, wherein the operating circuit for powering the heating element is selected based on the duty cycle of the pulse width modulation control circuit, and wherein the DC-DC control circuit including the DC-DC converter is selected when the duty cycle is greater than 85%.

16. The device of claim 13, wherein measuring the voltage over the heating element includes using a 3-wire connection or a 4-wire connection.

17. The device of claim 13, wherein the DC-DC converter includes a step-up and/or a step-down converter and an energy storage device, wherein the energy storage device includes an inductor and/or capacitors in a switched-capacitors topology or a charge-pump topology.

18. The device of claim 13, wherein measuring the voltage over the heating element occurs without interrupting power to the heating element.

19. The device of claim 13, wherein the DC-DC converter is configured to provide power uninterrupted to the heating element during a heating cycle.

20. The device of claim 13, further comprising an integrated circuit including the circuitry and the microcontroller.

* * * * *